US010646218B2

(12) United States Patent
Lee

(10) Patent No.: US 10,646,218 B2
(45) Date of Patent: May 12, 2020

(54) SURGICAL SUTURE PACKAGE

(71) Applicant: SM ENG. CO., LTD., Busan (KR)

(72) Inventor: Gil Soo Lee, Busan (KR)

(73) Assignee: SM ENG. CO., LTD., Busan (KR)

( * ) Notice: Subject to any disclaimer, the term of this patent is extended or adjusted under 35 U.S.C. 154(b) by 0 days.

(21) Appl. No.: 16/249,158

(22) Filed: Jan. 16, 2019

(65) Prior Publication Data

US 2019/0254662 A1  Aug. 22, 2019

(51) Int. Cl.
*A61B 17/06* (2006.01)
*A61B 90/94* (2016.01)
*A61B 90/90* (2016.01)
*A61B 17/00* (2006.01)

(52) U.S. Cl.
CPC .. *A61B 17/06133* (2013.01); *A61B 17/06114* (2013.01); *A61B 17/06119* (2013.01); *A61B 17/06123* (2013.01); *A61B 17/06138* (2013.01); *A61B 90/94* (2016.02); *A61B 90/90* (2016.02); *A61B 2017/00526* (2013.01); *A61B 2017/06142* (2013.01)

(58) Field of Classification Search
CPC .............. A61B 17/06133; A61B 90/94; A61B 2017/06142; A61B 17/06114; A61B 17/06138; A61B 17/06119; A61B 17/06123; A61B 90/90
USPC ...... 206/363, 63.3, 380, 382, 383, 438, 339, 206/574; 606/228, 232; 242/134, 141, 242/159
See application file for complete search history.

(56) References Cited

U.S. PATENT DOCUMENTS

| 5,180,053 | A  | * | 1/1993 | Cascio ............. A61B 17/06133 206/380 |
| 5,213,210 | A  | * | 5/1993 | Cascio ............. A61B 17/06133 206/380 |
| 6,854,598 | B2 | * | 2/2005 | Koseki ................... A01K 97/06 206/380 |
| 9,622,743 | B2 | * | 4/2017 | Kirsch ............. A61B 17/06133 |
| 2009/0205987 | A1 | * | 8/2009 | Kennedy .......... A61B 17/06133 206/363 |

(Continued)

FOREIGN PATENT DOCUMENTS

DE  69721880 T2  3/2004
EP     0608138 A2  7/1994

(Continued)

*Primary Examiner* — Rafael A Ortiz
(74) *Attorney, Agent, or Firm* — Novick, Kim & Lee, PLLC; Jae Youn Kim

(57) ABSTRACT

The surgical suture package includes: a main body including a base plate, an outer wall portion, and an inner wall portion providing a portion accommodating a suture; a fixing clip serving to fasten a suture needle coupled to an end of the suture; multiple protruding bumps; and multiple cover members provided on an upper portion of the inner wall portion, and configured to cover above the suture in a manner being bent outward and being hooked on lower surfaces of the protruding bumps to keep being bent such that the suture accommodated in the accommodating portion is prevented from being released, wherein a label is provided on an upper part of the main body to provide product information including a product name and is fastened by inserting an edge thereof between the protruding bumps and the cover members.

4 Claims, 6 Drawing Sheets

(56) References Cited

U.S. PATENT DOCUMENTS

| | | | |
|---|---|---|---|
| 2011/0215005 A1* | 9/2011 | Cerwin | A61B 17/06133 206/63.3 |
| 2012/0055828 A1* | 3/2012 | Kennedy | A61B 17/06133 206/363 |
| 2012/0150200 A1 | 6/2012 | Mitelberg et al. | |
| 2015/0366559 A1* | 12/2015 | Lee | A61B 17/06133 206/63.3 |

FOREIGN PATENT DOCUMENTS

| | | |
|---|---|---|
| EP | 1214912 A2 | 6/2002 |
| JP | 06-179477 A | 6/1994 |
| JP | 06-339480 A | 12/1994 |
| JP | 2014-519880 A | 8/2014 |
| JP | 2016-002463 A | 1/2016 |
| KR | 10-1488777 B1 | 2/2015 |
| KR | 10-2015-0085703 A | 7/2015 |

\* cited by examiner

SURGICAL SUTURE PACKAGE

CROSS REFERENCE TO RELATED APPLICATION

The present application claims priority to Korean Patent Application NO. 10-2018-0019146, filed Feb. 19, 2018 (2018.02.19), the entire contents of which is incorporated herein for all purposes by this reference.

BACKGROUND OF THE INVENTION

Field of the Invention

The present invention relates to a surgical suture package. More particularly, the present invention relates to a surgical suture package being configured such that a suture can be manually wound, thereby not requiring an expensive automatic apparatus for winding a suture and thus reducing manufacturing cost, configured such that occurrence of friction and jamming is reduced in a pulling process of a wound suture, thereby improving ease of use, and configured such that a label for displaying a product is fixed without using an adhesive.

Description of the Related Art

Generally, a surgical suture is a thread used to close a surgical opening caused by a wound or a surgery. Therefore, a surgical suture is required to be made of a material which is absorbed or not absorbed in a human body and excellent in elasticity and durability and thus not easily cut. A suture is generally stored in a sterile package opened at a surgical site such that the suture is pulled out of the package to suture a skin tissue. At one end of the suture, a suture needle is provided to constitute one set.

A suture package enables storing and carrying the suture in a sterile state and the suture is pulled out and used if necessary. The suture package has undergone much progress from the past, and in recent years, various types of suture packages have been proposed. There is a related art "suture case" disclosed in Korean Patent Application Publication No. 10-2015-0085703, published on Jul. 24, 2015. The suture case includes: a body portion having a space for winding a suture; and a lid portion engaged with the body portion, and a suture is wound around the body portion and then the lid portion is engaged therewith. In order to wind the suture in the space provided in the body portion, the suture is automatically wound by an automatic apparatus since winding the suture manually in a limited space is not efficient. Since winding the suture is required using an expensive automatic apparatus, the manufacturing cost is increased. In addition, a precise operation is demanded but the operation of winding the suture within a limited narrow space causes a high defect rate although the automatic apparatus is used. Furthermore, the case is configured into a two-piece type including the body portion and the lid portion such that there is a disadvantage in that jamming in a joint portion frequently occurs in the process of pulling out the wound suture.

Accordingly, there is a need for a suture package having a configuration in which a suture can be easily wound manually without using an expensive automatic machine such that the manufacturing cost can be reduced and the wound suture can be easily unwound.

SUMMARY OF THE INVENTION

Accordingly, the present invention has been made keeping in mind the above problems occurring in the related art, and the present invention is intended to provide a surgical suture package being configured such that a suture can be manually wound, thereby not requiring an expensive automatic apparatus for winding a suture and thus reducing a manufacturing cost, configured such that occurrence of friction and jamming is reduced in a pulling process of a wound suture, thereby improving ease of use, and configured such that a label for displaying a product is fixed without using an adhesive.

In order to achieve the above objective, there is provided a surgical suture package including: a main body including a base plate, an outer wall portion extending upward along an outer edge of the base plate, and an inner wall portion configured inside the inner wall portion in a manner extending upward to provide an accommodating portion accommodating a suture; a fixing clip provided on an inner surface of the base plate and serving to fasten a suture needle coupled to an end of the suture; multiple protruding bumps provided on an upper inner surface of the outer wall portion in a manner being spaced a predetermined distance apart from each other; and multiple cover members provided on an upper portion of the inner wall portion in a manner being spaced a predetermined distance apart from each other, and configured to cover above the suture in a manner being bent outward and being hooked on lower surfaces of the protruding bumps to keep being bent such that the suture accommodated in the accommodating portion is prevented from being released. A label is provided on an upper part of the main body to provide product information including a product name and is fastened by inserting an edge thereof between the protruding bumps and the cover members.

Multiple insertion holes may be provided in a bottom surface of the accommodating portion of the main body in a manner corresponding to a shape of the accommodating portion such that jigs are inserted therein and used to support the suture during winding thereof.

Multiple protruding ribs may be provided on a curved portion of the inner wall portion such that the suture wound and accommodated in the accommodating portion is not directly brought into close contact with an inner wall to reduce friction during unwinding of the suture.

The accommodating portion may be configured in an elliptical shape.

According to the present invention, with a structural improvement of a surgical suture package, an operator can easily wind a suture manually from the outside of an accommodating portion by using jigs or cover members formed on an upper portion of an inner wall whereby the work efficiency is improved. In addition, an expensive automatic apparatus is not required whereby manufacturing cost can be reduced. In addition, an edge of a label providing product information is inserted between protruding bumps and cover members to be fastened easily, thereby improving ease of work.

Furthermore, the package is configured into an integrated body such that occurrence of friction and jamming is reduced in a pulling process of a suture, thereby improving ease of use.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, a surgical suture package of the present invention will be described in detail with reference to the accompanying drawings.

Terms or words used in the specification and claims are not limited to a meaning that is commonly understood by people or is defined in dictionaries, and should be interpreted as having a meaning that is consistent with meaning in the context of the relevant art.

Therefore, the description proposed herein is just a preferable example for the purpose of illustrations only and is not intended to limit the scope of the disclosure, so it should be understood that other equivalents and modifications could be made thereto without departing from the spirit and scope of the disclosure.

Figure 1:
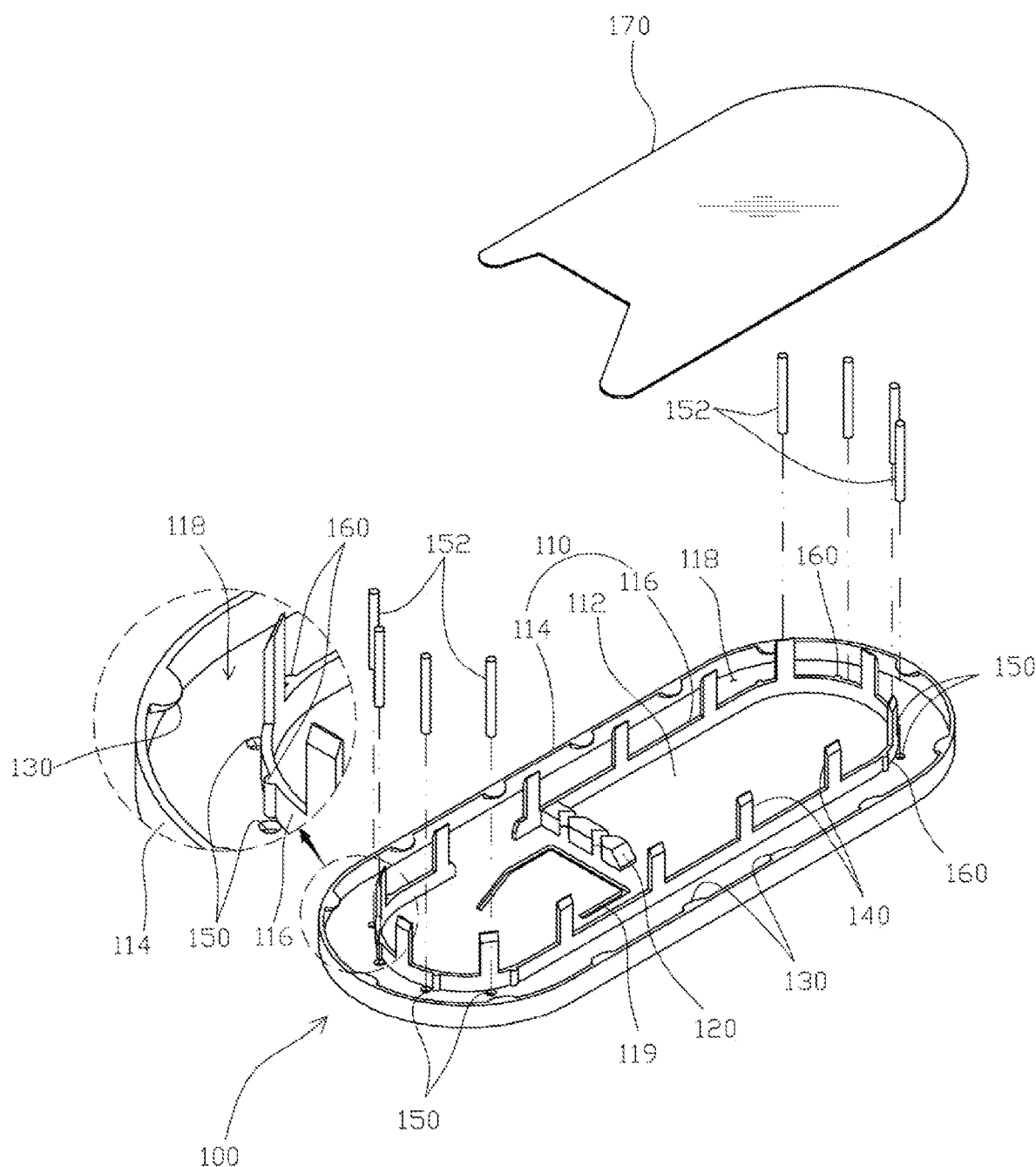
FIG. 1 is a perspective view illustrating a surgical suture package according to an embodiment of the present invention.
Figure 2A:
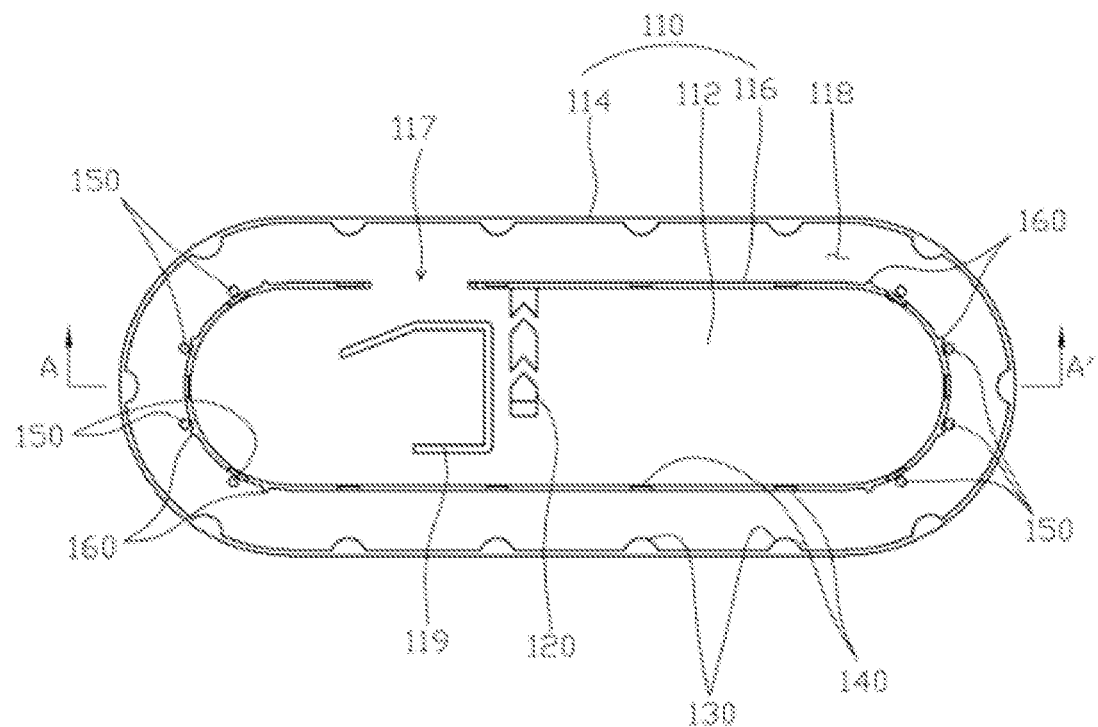
FIG. 2A is a plan view illustrating the surgical suture package according to the embodiment of the present invention.

FIG. 1 is a perspective view illustrating a surgical suture package according to an embodiment of the present invention; FIG. 2A is a plan view illustrating the surgical suture package according to the embodiment of the present invention; and FIG. 2B is a vertical cross-sectional view of FIG. 2A taken along line A-A'.

Figure 2B:
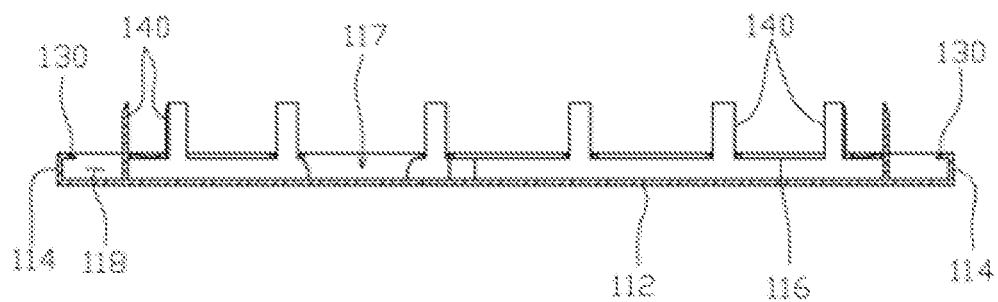
FIG. 2B is a vertical cross-sectional view of FIG. 2A taken along line A-A'.

As illustrated in FIGS. 1, 2A, and 2B, a surgical suture package 100 of the present invention is configured into an integrated body and used to store, carry, and pull out a surgical suture. Specifically, the surgical suture package 100 includes a main body 110, a fixing clip 120, protruding bumps 130, and cover members 140, and may further include a label 170.

The main body 110 includes: a base plate 112 having an elliptical shape; an outer wall portion 114 extending upward along an outer edge, i.e., a rim of the base plate 112 and having a predetermined height; and an inner wall portion 116 configured inside the outer wall portion 114 in a manner extending upward along a form of the outer wall portion 114 to provide an accommodating portion 118 accommodating a suture between the outer wall portion 114 and the inner wall portion 116.

A cutout 117 is formed on a side portion of the inner wall 116 to allow the accommodating portion 118 and the inside of the base plate 112 to communicate with each other. Thus, the suture, which is not illustrated here, smoothly communicates the inside and outside through the cutout 117. A cutout groove 119 is formed on an upper surface of the base plate 112 and cut into a substantially U shape. The cutout groove 119 is configured such that a part of the base plate 112 is easily moved up and down whereby it is possible to easily catch a suture needle using a medical instrument such as a forceps or the like.

Here, it is preferable that the base plate 112 is configured in an elliptical shape, but it should be understood that a shape of the base plate 112 is not limited thereto. The base plate 112 may be configured in a rectangular shape or a square shape. Even when the base plate 112 is configured in a shape other than an elliptical shape, it is preferable that the accommodating portion 118 formed between the outer wall portion 114 and the inner wall portion 116 is configured in an elliptical shape.

The fixing clip 120 is formed in a central portion of the base plate 112 of the main body 110, and configured with a fitting hollow in which the suture needle coupled to the end of the suture is inserted and fastened. The fixing clip 120 is formed at a side portion of the cutout groove 119 formed in the base plate 112 such that a part of the suture needle is fastened to the fixing clip 120 via the cutout groove 119. Thus, using in that a part of the base plate 112 is bent by the incision groove 119, the suture needle can be easily picked up.

The multiple protruding bumps 130 are formed on an upper inner surface of the outer wall portion 114 defining the outer wall of the base plate 112 in a manner being spaced a predetermined distance apart from each other. It is obvious that the protruding bumps 130 may have an irregular distance, and may have various shapes such as a half-moon shape, a polygonal shape, or the like.

The multiple cover members 140 are formed on an upper surface of the inner wall portion 116 forming the inner wall of the base plate 112 in a manner being spaced a predetermined distance apart from each other. It is preferable that the cover members 140 are formed in the same number and distance as the protruding bumps 130. In addition, the cover members 140 are configured to cover the suture in a manner being bent outward and being hooked on lower surfaces of the protruding bumps 130 disposed at positions corresponding to the ends of the cover members 140 to keep being bent such that the suture accommodated in the accommodating portion 118 is prevented from being released upward.

Here, it is preferable that an upper end portion of each cover member 140 is made thinner than a remaining portion thereof to increase the flexibility such that the operation of engaging with each protruding bump 130 is smoothly performed.

As illustrated in the enlarged view of FIG. 1, multiple insertion holes 150 are formed in the bottom surface of the accommodating portion 118 of the main body 110 such that jigs 152 are inserted and used to support the suture during winding of the suture. The multiple insertion holes 150 may be formed corresponding to the shape of the accommodating portion 118, and preferably, formed on only curved portions of both sides of the accommodating portion 118.

In addition, multiple protruding ribs 160 are formed on the curved surface of the inner wall portion 116 in a manner protruding into the space of the accommodating portion 118 such that the suture wound and accommodated in the accommodating portion 118 is not directly brought into close contact with the inner wall to reduce friction during unwinding of the suture.

The label 170 provides various product information including a name of the product. In general, the label 170 is attached to an upper part of the main body 110 by using an adhesive, but in the present invention, the label 170 is attached in a different manner that will be described below.

Figure 3:
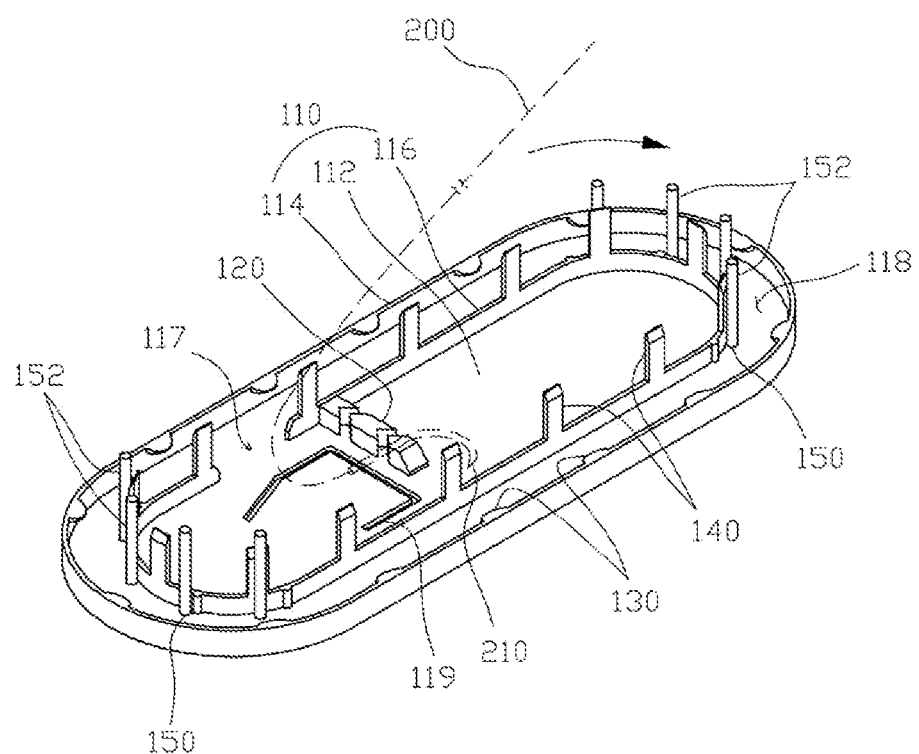
FIG. 3 is a perspective view of the surgical suture package, which illustrates a process of preparing to wind a suture according to the embodiment of the present invention.
Figure 4A:
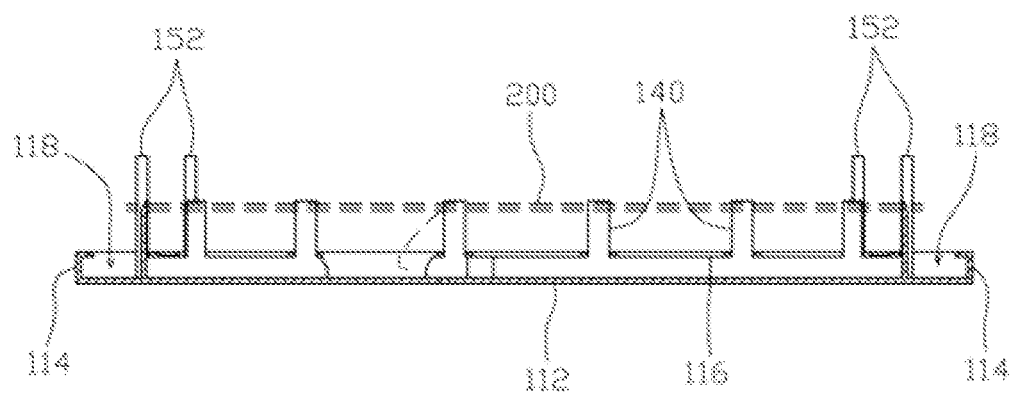
FIGS. 4A to 4C are vertical cross-sectional views sequentially illustrating a process of winding the suture according to the embodiment of the present invention.
Figure 4B:
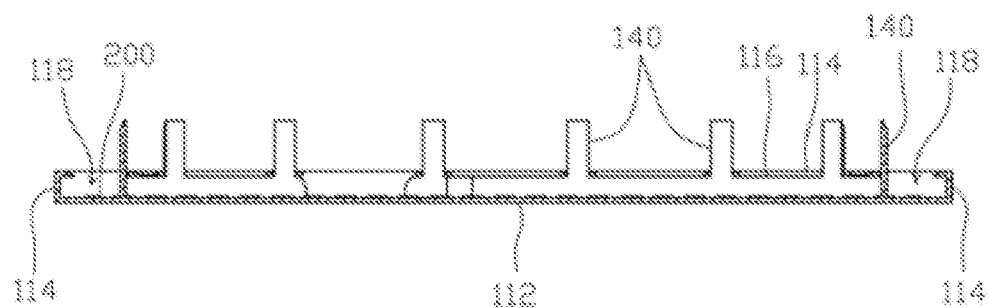
Figure 4C:
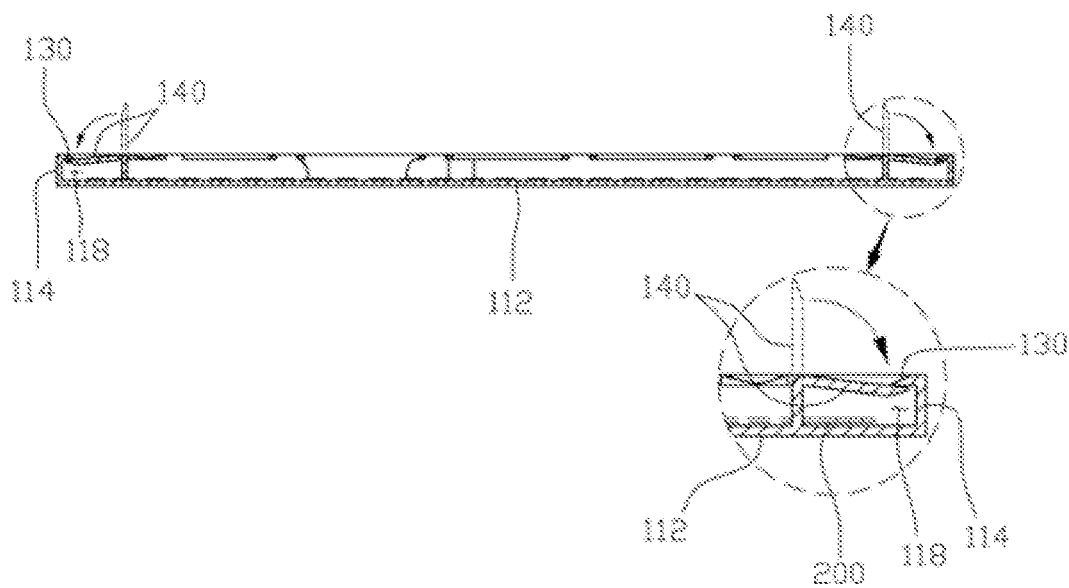
Figure 5:
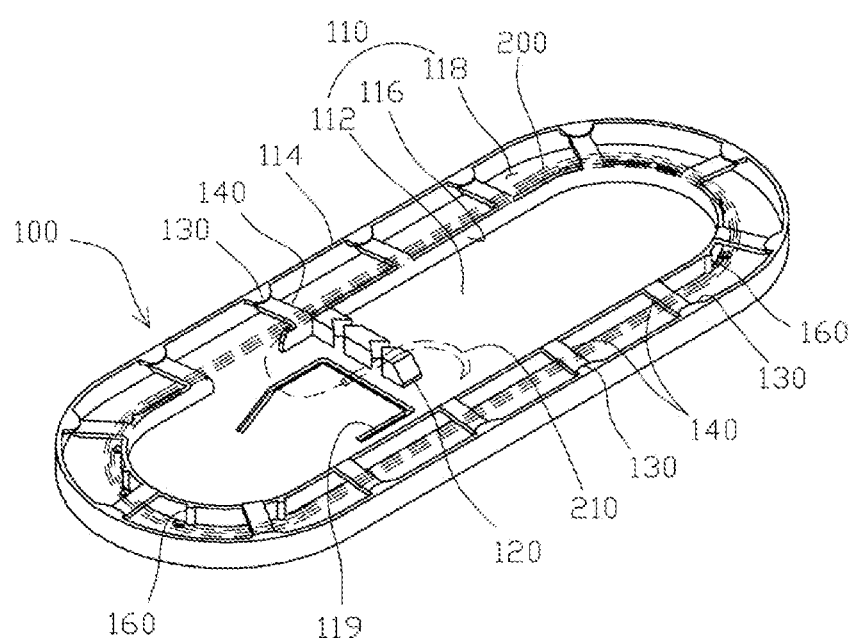
FIG. 5 is a perspective view illustrating the surgical suture package in which the suture is wound according to the embodiment of the present invention.
Figure 6:
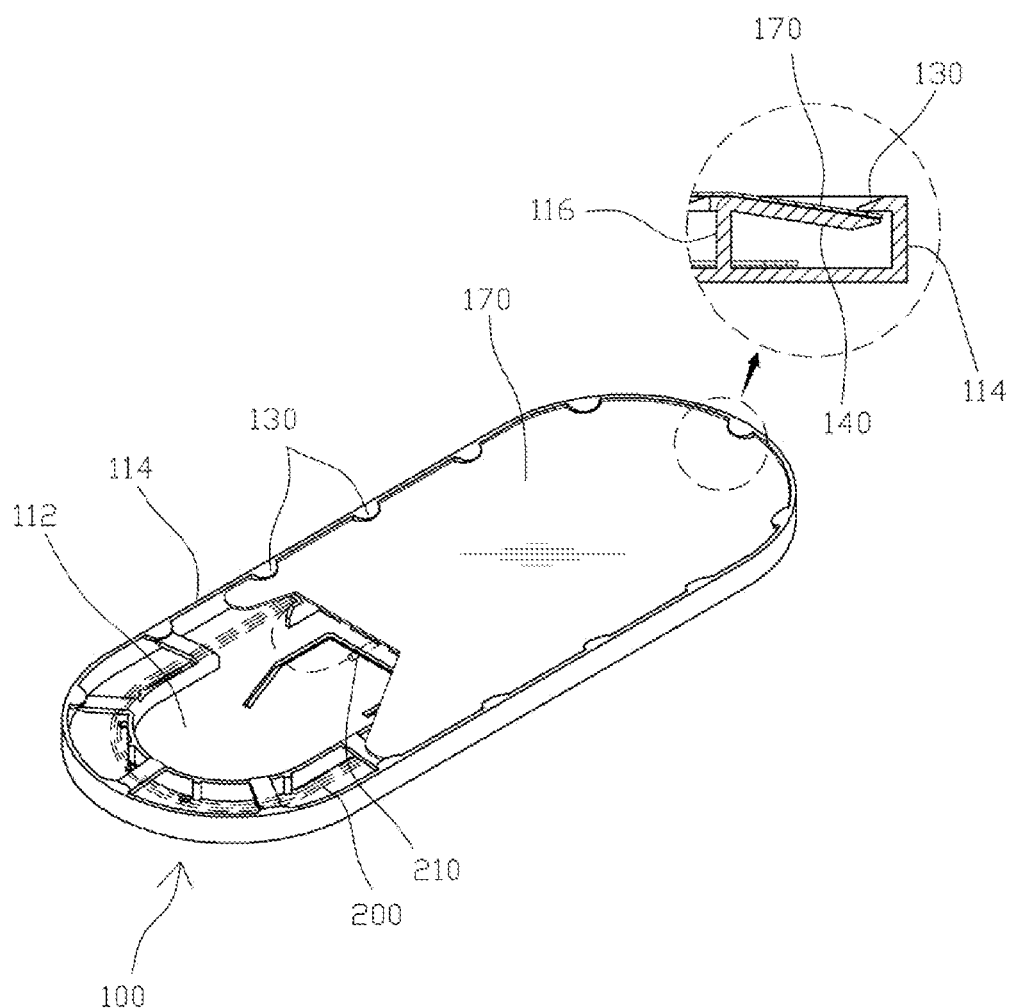
FIG. 6 is a perspective view illustrating the surgical suture package on which a label is provided according to the embodiment of the present invention.

FIG. 3 is a perspective view of the surgical suture package, which illustrates a process of preparing to wind a suture according to the embodiment of the present invention; FIGS. 4A to 4C are vertical cross-sectional views sequentially illustrating a process of winding the suture according to the embodiment of the present invention; FIG. 5 is a perspective view illustrating the surgical suture package in which the suture is wound according to the embodiment of the present invention; and FIG. 6 is a perspective view illustrating the surgical suture package on which a label is provided according to the embodiment of the present invention.

As illustrated in FIG. 3, in order to wind a suture 200 around the main body 110, preparing for winding the suture 200 is performed such that the long pole-shaped jigs 152 are respectively inserted into the insertion holes 150 formed in the both curved sides of the bottom surface of the receiving portion 118, a suture needle 210 coupled to the end of the suture 200 is inserted and fastened to the fixing clip 120 provided on the bottom surface of the base plate 112, and the suture 200 is passed to the accommodating portion 118 through the cutout 117 of the inner wall portion 116. Although the conventional method of fastening the suture needle 210 to wind the suture 200 is illustrated in the drawing, it is obvious that the opposite order in which the suture 200 is wound and then the suture needle 210 is fastened to the fixing clip 120 is possible.

When preparing for winding the suture 200 is completed, as illustrated in FIG. 4A, the suture 200 is wound around an outer surface of the jigs 152 provided on both sides of the accommodating portion 118. Here, when the jigs 152 are not used, the suture 200 is wound on an outer surface the multiple cover members 140 formed on the inner wall portion 116.

When the suture 200 is completely wound, as illustrated in FIG. 4B, the suture 200 wound around the jigs 152 is put down and accommodated in the accommodating portion 118 of the main body 110, and the jigs 152 are separated from the insertion holes 150. As illustrated in FIG. 4C, the multiple cover members 140 formed on the upper portion of the inner wall portion 116 are bent outward such that the ends thereof are positioned on the lower surfaces of the protruding bumps 130 formed on the outer wall portion 114 and kept being bent. Then, as illustrated in FIG. 5, as the multiple cover members 140 partially cover an opened top portion of the accommodating portion 118, the suture 200, which is positioned in the accommodating portion 118 while being wound around the receiving portion 118, is prevented from being released outside.

Since the jigs 152 or the cover members 140 can be used when winding the suture 200 rather than directly winding the suture 200 in the narrow space of the accommodating portion 118, an operator can winds a suture manually whereby an expensive automatic apparatus is not required and thus the manufacturing cost can be greatly reduced.

Here, in order to pull out the wound suture 200, the suture needle 210 is caught using a medical instrument such as forceps and pulled in a diagonal direction as is well known in the art. In the case of catching the suture needle 210, since the base plate 112 is partly opened through the cutout groove 119 112, the suture needle 210 can be easily caught. Particularly, since the package 100 of the present invention is configured into an integrated body, a joint portion or a gap is not generated such that jamming of the suture 200 in a joint portion or a gap during pulling out the suture 200 can be prevented fundamentally. In addition, the protruding ribs 160 are formed on the curved surface portion of the inner wall portion 116 where friction is frequently generated, thereby reducing the friction surface and thus minimizing the occurrence of friction. Accordingly, the suture 200 can be easily pulled out.

When bending and fastening the cover members 140 after winding the suture 200 is completed, the label 170 is provided on an upper part of the main body 110 to provide product information including a product name as illustrated in FIG. 6. Unlike the conventional case where the label 170 is attached using an adhesive, the label 170 is fastened by inserting an edge thereof between the protruding bumps 130 formed on the outer wall portion 114 and the cover members 140 disposed on the lower surfaces of the protruding bumps 130 as illustrated in a partially enlarged view of FIG. 6. Thus, the adhesive is unnecessary, leading to convenient operation, and the label 170 can be easily separated, thereby improving the ease of use.

It is obvious that the product is distributed through a process in which the label 170 is provided as described above, a sterilizing process is performed, and the package is wrapped in a wrapping paper.

The foregoing has outlined rather broadly the features and technical advantages of the present invention in order that the claims of the invention to be described below may be better understood.

What is claimed is:

1. A surgical suture package comprising:
   a main body including a base plate, an outer wall portion extending upward along an outer edge of the base plate, and an inner wall portion disposed inside the outer wall portion and extending upward to provide an accommodating portion capable of accommodating a suture between the outer wall portion and the inner wall portion;
   a fixing clip disposed on an inner surface of the base plate and configured to fasten a suture needle coupled to an end of the suture;
   a plurality of protruding bumps disposed on an upper inner surface of the outer wall portion and spaced apart from each other;
   a plurality of cover members disposed on an upper portion of the inner wall portion and spaced apart from each other, and configured to cover above the suture by being bent outward and being hooked on lower surfaces of the protruding bumps such that the suture accommodated in the accommodating portion is prevented from being released, wherein an upper end portion of each of the plurality of cover members is thinner than a remaining portion thereof to increase flexibility; and
   a label configured to be disposed on an upper part of the main body to provide product information including a product name, the label being fastened by inserting an edge thereof between the protruding bumps and the cover members, wherein the edge of the label is directly in contact with both the protruding bumps and the cover members.

2. The surgical suture package of claim 1, wherein a plurality of insertion holes are disposed in a bottom surface of the accommodating portion of the main body such that a plurality of jigs are inserted therein and used to support the suture during winding thereof.

3. The surgical suture package of claim 1, wherein a plurality of protruding ribs are disposed on a curved portion of the inner wall portion such that the suture wound and accommodated in the accommodating portion is not directly brought into close contact with an inner wall to reduce friction during unwinding of the suture.

4. The surgical suture package of claim 1, wherein the accommodating portion is in an elliptical shape.

\* \* \* \* \*